United States Patent [19]

Albrecht et al.

[11] 3,950,265

[45] Apr. 13, 1976

[54] DISPERSIONS OF 2-ALKYL-4,6-DINITROPHENOL ESTERS

[75] Inventors: Konrad Albrecht, Fischbach, Taunus; Heinz Frensch, Frankfurt am Main, both of Germany

[73] Assignee: Hoechst Aktiengesellschaft, Frankfurt am Main, Germany

[22] Filed: Mar. 27, 1974

[21] Appl. No.: 455,327

[30] Foreign Application Priority Data

Mar. 29, 1973 Germany............................ 2315641

[52] U.S. Cl. .................... 252/311; 71/106; 71/107; 252/320; 424/301; 424/305; 424/308; 424/311
[51] Int. Cl.²......................................... B01J 13/00
[58] Field of Search ...... 71/106, 107; 424/301, 311, 424/314; 260/463, 476 R, 479 R, 468 R; 252/311, 326.5

[56] References Cited
UNITED STATES PATENTS

| | | | |
|---|---|---|---|
| 2,861,915 | 11/1958 | Cary | 424/314 |
| 2,862,022 | 11/1958 | Cook et al. | 260/479 R |
| 3,198,824 | 8/1965 | van den Boogaart | 260/463 |
| 3,412,132 | 11/1968 | Pianka et al. | 424/301 X |
| 3,453,318 | 7/1969 | Pianka | 260/479 R |
| 3,718,454 | 2/1973 | Albrecht | 71/106 |
| 3,728,458 | 4/1973 | Pianka | 424/311 |
| 3,759,972 | 9/1973 | Pianka | 260/463 |

*Primary Examiner*—Joseph P. Brust
*Attorney, Agent, or Firm*—Curtis, Morris & Safford

[57] ABSTRACT

Stabilized aqueous dispersions of 2-alkyl-4,6-dinitrophenol esters, which comprise certain metal complex dyestuffs from the series of the azo dyestuff or phthalocyanine dyestuff complexes.

2 Claims, No Drawings

DISPERSIONS OF 2-ALKYL-4,6-DINITROPHENOL ESTERS

The present invention relates to stabilized aqueous dispersions of 2-alkyl-4,6-dinitrophenol esters which are known as fungicides and/or acaricides or herbicides.

Well known members of this class are for example dimethylacrylic acid -(4,6-dinitro-2-sec.-butylphenyl) ester (binapacryl) and carbonic acid isopropyl-(4,6-dinitro-2-sec.-butylphenyl) ester (dinobuton), a carbonic acid diester.

The preparation of aqueous dispersions of such compounds has already been described (see for example German Offenlegungsschrift No. 1,912,707). Such dispersions are stable for a short period but on prolonged storage display a considerable tendency to crystal growth, which is due to a certain, though very slight, solubility of the 2-alkyl-4,6-dinitrophenol esters in water. Because of their higher solution pressure, the little particles at the lower end of the size-distribution curve dissolve first, thus forming a saturated solution from which the active substance slowly crystallizes again, this time adhering to the larger undissolved crystals. In this manner, in commerical dispersions, where the active substances originally have grain sizes usually below 10 microns, crystals having a length of up to 50 microns are often formed after a storage period of from 2 to 3 months.

A particle growth of active substance and a simultaneous decrease of their number of course result in a quality decrease of the dispersion and also in a decrease of the biological activity. It is therefore the object of the present invention to provide a means to stabilize the particles of active substance in such dispersions against undesired crystal growth.

This object is accomplished according to the present invention by adding a metal complex dyestuff of the group consisting of azo and phthalocyanine metal complex dyestuffs in concentrations of from 0.1 to 3, preferably from 0.3 to 1 % by weight, to such aqueous dispersions.

Suitable metal complex dyestuffs are for example water-soluble sulfonamide group containing 2:1 monoazo metal complex dyestuffs obtained by coupling optionally substituted β-naphthols or substituted pyrazolones with sulfonamide group containing hydroxyanilines also optionally substituted, and which contain cobalt or chromium as central metal atoms. Compounds of this kind are for example described in German Auslegeschrift No. 1,016,866 and U.S. Pat. No. 2,610,175. An example is the dyestuff known as Acid Blue 199, a 2:1 monoazo dyestuff/chromium complex.

Suitable are also water-insoluble laked sulfo group containing azo dyestuffs obtained by coupling naphtols optionally substituted by carboxylic acid and/or sulfonic acid groups, especially β-naphthol, with anilinesulfonic acids optionally substituted (preferably by —CH$_3$, —COOH and/or CL), or naphthylamines and subsequent laking with metal salts (see Venkataraman, The Chemistry of Synthetic Dyes, New York 1952, Vol. I, p. 486). As central metal atom they contain preferably barium, calcium and manganese; especially advantageous are BA-compounds. Examples of such sulfo group containing azo dyestuffs, which are then laked with metal salts, are the following dyestuffs listed in The Colour Index (C.I.): Lake Pigment Red 53 (C.I. No. 15 585), Lake Pigment Red 68 (C.I. No. 15 525), Lake Pigment Red 57 (C.I. No. 15 850) or Lake Pigment Red 54 (C.I. No. 14 830).

Furthermore, phthalocyanine dyestuffs in which the phthalocyanine skeleton is either unsubstituted or substituted by chlorine or bromine, are also suitable. Such complexes contain preferably copper, cobalt or iron as central atoms. Examples are C.I. Pigment Blue 15 (C.I. No. 74 160), a copperphthalocyanine, Pigment Green 7 (C.I. No. 74 260), a polyhalogenated copperphthalocyanine, and cobalt-phthalocyanine.

Of course, the problem of crystal growth arises only in the case of such 2-alkyl-4,6-dinitrophenol esters which are solid at the temperatures of grinding and storage, that is, generally in the case of 2-alkyl-4,6-dinitrophenol esters having melting points above 30°C, preferably above 50°C. Such compounds are above all those having the following formula

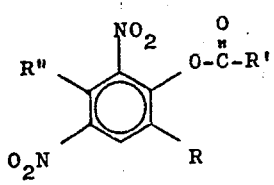

where R is alkyl having from 1 to 5 carbon atoms, or cycloalkyl having 5 or 6 carbon atoms, R' is alkyl or o-alkyl having from 1 to 4 carbon atoms, alkenyl having from 2 to 4 carbon atoms or the phenyl or cyclohexyl radical, and R'' is methyl or preferably hydrogen.

R can be a straight-chain group, especially methyl, or preferably a branched group, for example sec.-butyl or tert.-butyl, and R' can be methyl, ethyl, propyl, isopropyl, butyl, vinyl, dimethylvinyl, methoxy, ethoxy, propyloxy, isopropyloxy.

Known examples of such compounds are [4,6-dinitro-2-sec.-butylphenol]-dimethylacrylic acid ester (binapacryl), the corresponding isopropylcarbonic acid ester (dinobuton), the corresponding benzoic or hexahydrobenzoic acid ester, furthermore [4,6-dinitro-2-tert.-butylphenol]-acetic acid ester, [4,6-dinitro-2-tert.-butyl-5-methylphenol]-acetic acid ester, and furthermore the [4,6-dinitro-2-sec.-butylphenol]-trimethylacetic acid or -(ethylcarbonic acid) ester.

Suitable dispersing agents used in the aqueous suspensions of the invention are especially the different cellulose pitch types (sodium, calcium and ammonium salts of ligninsulfonic acid), sodium salts of dinaphthylmethane-disulfonic acid, and alkali metal or ammonium salts of polymer alkylsulfonic acids. Especially usful are the commercial dispersing agents Vaniperse CB (sodium-oxylignin sulfonate) or Darvan No. 3 (sodium-polyalkyl sulfonate). The amount of dispersing agent used is from 2 to 5 %.

The following examples illustrate the invention.

EXAMPLE 1

(Comparative Example)

In a grinding ball mill containing quartz balls having a diameter of 2 mm as grinding elements, a dispersion of the following composition was ground to a grain size of below 4 microns:

| | | |
|---|---|---|
| 50 | weight % of | binapacryl, technical grade |
| 2 | do. | Vanisperse CB⁽ᴿ⁾ |
| 0.8 | do. | Darvan No. 3⁽ᴿ⁾ |
| 1.0 | do. | Acid Blue 199 |
| 46.2 | do. | water |

The dispersion had a relatively low viscosity and was easily pourable. The grain distribution spectrum remained the same even after a prolonged storage period or under severe storage conditions at 50°C for more than 3 months. The average grain size was then about 6 microns.

When the dispersion according to this example was prepared without the addition of a stabilizer, there occurred a crystal growth of the binapacryl with simultaneous increase of viscosity during storage. Already after a 6 to 8 week storage, crystals of from 30 to 50 microns were detectable. Some technical grade batches of binapacryl even tended to sedimentation.

EXAMPLE 2

According to Example 1, a dispersion of the following composition were prepared:

| | | |
|---|---|---|
| 50 | weight % of | binapacryl, technical grade |
| 2 | do. | Vanisperse CB⁽ᴿ⁾ |
| 0.8 | do. | Darvan No. 3⁽ᴿ⁾ |
| 1.0 | do. | C.I. Pigment Blue 15 (C.I. No. 74 160) |
| 46.2 | do. | water |

The stabilization effect was the same as in Example 1.

EXAMPLE 3

According to Example 1, a dispersion of the following composition was prepared:

| | | |
|---|---|---|
| 50 | weight % of | binapacryl, technical grade |
| 2 | do. | Vanisperse CB⁽ᴿ⁾ |
| 0.8 | do. | Darvan No. 3⁽ᴿ⁾ |
| 0.5 | do. | C.I. Pigment Red 53:1 (Ba salt)(C.I. No. 15 585 : 1) |
| 46.7 | do. | water |

The stabilization effect was the same as in Example 1.

EXAMPLE 4

According to Example 1, a dispersion of the following composition was prepared:

| | | |
|---|---|---|
| 50 | weight % of | binapacryl, technical grade |
| 2 | do. | Vanisperse CB⁽ᴿ⁾ |
| 0.8 | do. | Darvan No. 3⁽ᴿ⁾ |
| 1.0 | do. | cobalt-phthalocyanine |
| 46.2 | do. | water |

The stabilization effect was the same as in Example 1.

EXAMPLE 5

According to Example 1, a dispersion of the following composition was prepared:

| | | |
|---|---|---|
| 50 | weight % of | binapacryl, technical grade |
| 3 | do. | Vanisperse CB⁽ᴿ⁾ |
| 0.8 | do. | Darvan No. 3⁽ᴿ⁾ |
| 1.0 | do. | Hostaperm Green GG (polychlorinated Cu-phthalocyanine) |
| 45.2 | do. | water |

Also in this case, the crystal growth of the binapacryl was prevented.

EXAMPLE 6

In a grinding ball mill containing quartz balls having a diameter of 2 mm as grinding elements, a dispersion of the following composition was ground to a grain size of below 5 microns:

| | | |
|---|---|---|
| 50 | weight % of | dinobuton, technical grade |
| 5 | do. | Vanisperse CB⁽ᴿ⁾ |
| 0.2 | do. | Tamol NNO⁽ᴿ⁾ (sodium salt of dinaphthyl-methane-disulfonic acid) |
| 0.6 | do. | Darvan No. 3⁽ᴿ⁾ |
| 46.2 | do. | water |

The dispersion obtained was well flowable. When stored at 50°C, considerable crystal growth after 4 to 6 weeks took place resulting in a deterioration of the physical properties and decrease of the biological activity.

EXAMPLE 7

The crystal growth can be prevented when 0.8 weight % of C.I. pigment Blue 15 is added to the dispersion of Example 6 before grinding:

| | | |
|---|---|---|
| 50 | weight % of | dinobuton, technical grade |
| 3 | do. | Vanisperse CB⁽ᴿ⁾ |
| 0.2 | do. | Tamol NNO⁽ᴿ⁾ |
| 0.6 | do. | Darvan No. 3⁽ᴿ⁾ |
| 0.8 | do. | C.I. Pigment Blue 15 (Cu-phthalocyanine) |
| 45.4 | do. | water |

EXAMPLE 8

When operating as indicated in Example 7, but replacing Pigment Blue by Lake Pigment Red 57 (C.I. No. 15 850), the crystal growth of dinobuton in aqueous dispersions was prevented. An aqueous dispersion of the following composition

| | | |
|---|---|---|
| 40 | weight % of | dinobuton |
| 3.5 | do. | Vanisperse CB⁽ᴿ⁾ |
| 0.3 | do. | Tamol NNO⁽ᴿ⁾ |
| 0.6 | do. | Darvan No. 3⁽ᴿ⁾ |
| 1.0 | do. | Lake Pigment Red 53 (Ba salt) |
| 54.6 | do. | water | showed a considerably retarded crystal growth as compared to Example 6.

EXAMPLE 9

Also the 4,6-dinitro-2-tert.-butylphenolacetic acid ester, in the form of its aqueous dispersion, showed an increased crystal growth, which can be retarded by adding Cu-phthalocyanine. When using the following composition:

| | | |
|---|---|---|
| 50 | weight % of | 4,6-dinitro-2-tert.-butylphenolacetic acid ester |
| 3 | do. | Vanisperse CB⁽ᴿ⁾ |
| 0.8 | do. | Darvan No. 3⁽ᴿ⁾ |
| 1.0 | do. | C.I. Pigment Blue 15 (C.I. No. 74 160) |
| 45.2 | do. | water | a stabilized dispersion was obtained after grinding according to Example 6.

What is claimed is:

1. Stabilized aqueous dispersions of 2-alkyl-4,6-dinitrophenol esters of the formula

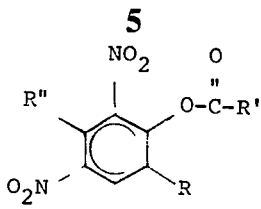

where R is alkyl of 1 to 5 carbon atoms or cycloalkyl of 5 or 6 carbon atoms, R' is alkyl or o-alkyl of 1 to 4 carbon atoms, alkenyl of 2 to 4 carbon atoms, phenyl or cyclohexyl, and R" is methyl or hydrogen, having a melting point above 30°C, which consists essentially of, in addition to water, said ester, and dispersing agent, from 0.1 to 3% by weight of a metal complex azo dyestuff selected from the group consisting of Acid Blue 199 (2:1 monoazo dyestuff/chromium complex) and azo dyestuff complexes obtained by laking Lake Pigment Red 53 (C.I. No. 15 585), Lake Pigment Red 68 (C.I. No. 15 525), Lake Pigment Red 57 (C.I. No. 15 850) or Lake Pigment Red 54 (C.I. No. 14 830) or a metal complex phthalocyanine dyestuff selected from the group consisting of Pigment Blue 15 (C.I. No. 74 160), Pigment Green 7 (C.I. No. 74 260) and cobaltphthalocyanine.

2. Stabilized aqueous dispersions as claimed in claim 1, wherein the 2-alkyl-4,6-dinitrophenol ester is [4,6-dinitro-2-sec.-butylphenol]-dimethylacrylic acid ester or the corresponding isopropylcarbonic acid, benzoic acid or hexahydrobenzoic acid ester, [4,6-dinitro-2-tert.-butylphenol]-acetic acid ester, [4,6-dinitro-2-tert.-butyl-5-methyl-phenol]-acetic acid ester, or [4,6-dinitro-2-sec.-butylphenol]-trimethylacetic acid ester or the corresponding ethylcarbonic acid ester.

* * * * *